(«12») United States Patent
Singhal

(10) Patent No.: US 9,757,062 B2
(45) Date of Patent: Sep. 12, 2017

(54) APPARATUS AND METHODS FOR A LANCET DEVICE FOR REUSE OF LANCETS FOR HOME-USERS

(76) Inventor: Tara Chand Singhal, Torrance, CA (US)

( * ) Notice: Subject to any disclaimer, the term of this patent is extended or adjusted under 35 U.S.C. 154(b) by 839 days.

(21) Appl. No.: 13/421,620

(22) Filed: Mar. 15, 2012

(65) Prior Publication Data

US 2013/0245660 A1 Sep. 19, 2013

(51) Int. Cl.
*A61B 17/32* (2006.01)
*A61B 5/15* (2006.01)
*A61B 5/151* (2006.01)

(52) U.S. Cl.
CPC .. *A61B 5/150328* (2013.01); *A61B 5/150022* (2013.01); *A61B 5/15105* (2013.01); *A61B 5/15186* (2013.01); *A61B 5/150412* (2013.01); *A61B 5/150183* (2013.01)

(58) Field of Classification Search
CPC ........ A61B 5/150412; A61B 5/150328; A61B 5/150183; A61B 5/150022
USPC .................................................. 606/181, 182
See application file for complete search history.

(56) References Cited

U.S. PATENT DOCUMENTS

| | | | | |
|---|---|---|---|---|
| 4,648,408 A | * | 3/1987 | Hutcheson et al. | 600/583 |
| 5,639,310 A | * | 6/1997 | Giampaolo, Jr. | 134/6 |
| 5,871,494 A | * | 2/1999 | Simons et al. | 606/181 |
| 2003/0153939 A1 | * | 8/2003 | Fritz et al. | 606/181 |
| 2005/0177072 A1 | * | 8/2005 | Kloepfer et al. | 600/583 |
| 2006/0282109 A1 | * | 12/2006 | Jansen et al. | 606/181 |
| 2009/0234246 A1 | * | 9/2009 | Usui | 600/583 |

* cited by examiner

*Primary Examiner* — Julie A Szpira
(74) *Attorney, Agent, or Firm* — Steve Roeder, Esq.

(57) ABSTRACT

A lancet device used for drawing a blood sample for testing has a lancet, a lancet holding mechanism, a lancet activation plunger, and a removable lancet cap with an opening for touching against the human body. The lancet has a needle, where the needle is movable inside the cap with the lancet activation plunger. The lancet device has positioned inside the device, a disinfectant material, disinfecting the lancet needle for each use. The disinfectant material lets the needle move or rest inside the disinfectant material disinfecting the needle between each use. The lancet needle moves through the disinfectant material when used, disinfecting the needle for each use.

20 Claims, 8 Drawing Sheets

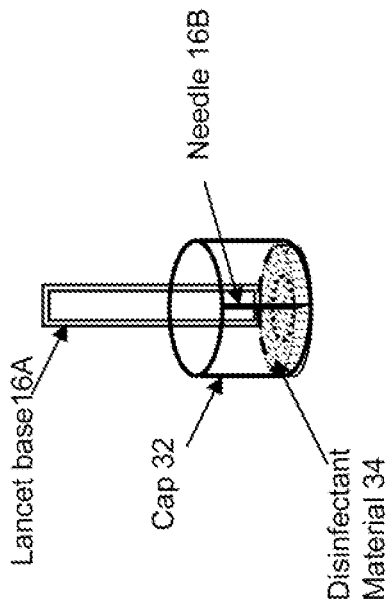
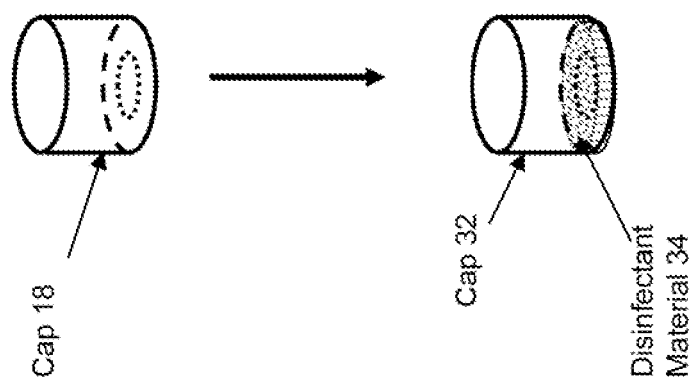
Figure 3B
Figure 3A

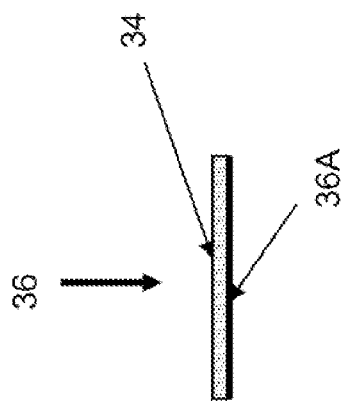
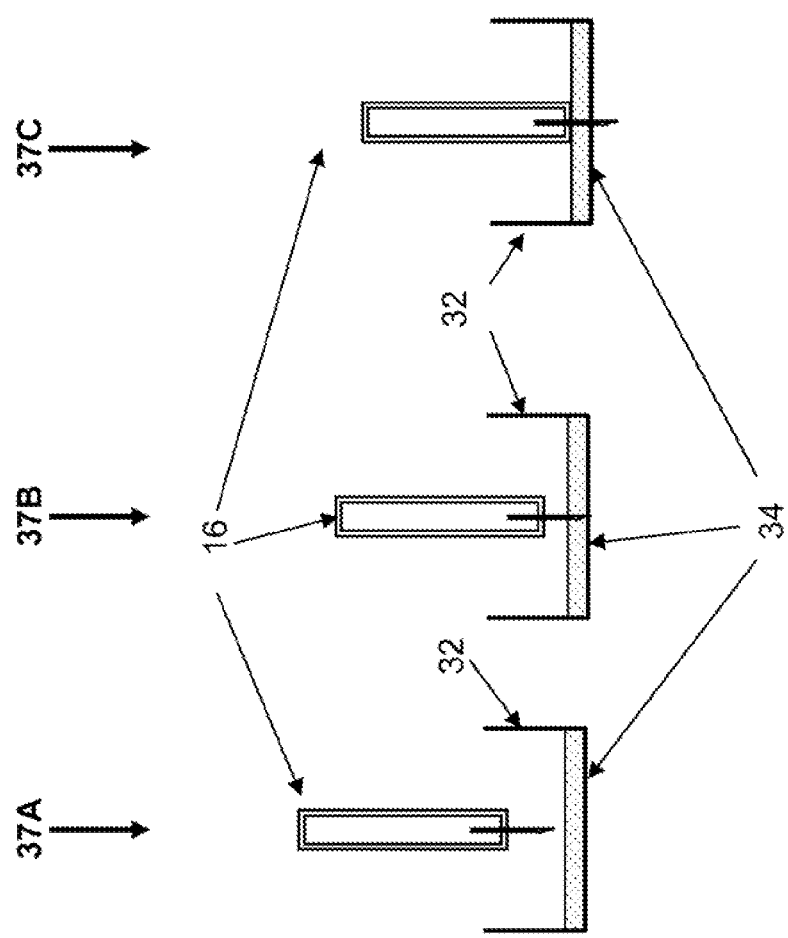
Figure 4B
Figure 4A

| | |
|---|---|
| positioning inside a lancet device, a disinfectant material, disinfecting the lancet needle for each use. | 100 |
| making the disinfectant material of sponge like material for holding a disinfectant and for moving or resting the needle inside the disinfectant material. | 102 |
| resting the lancet needle inside the disinfectant material, when not plunged, disinfecting the needle between each use. | 104 |
| moving the lancet needle through the disinfectant material when used, disinfecting the needle for each use. | 106 |
| shaping the disinfectant material as a disc for positioning inside the cap. | 108 |
| shaping the disinfectant material as a disc for positioning inside the cap, where the thickness of the disc is at least a 1 mm to 3 mm thick for positioning and moving the needle inside the disc. | 110 |
| shaping the disinfectant material as a disc and positioning the disc inside the cap at the bottom of the cap. | 112 |

Figure 6

APPARATUS AND METHODS FOR A LANCET DEVICE FOR REUSE OF LANCETS FOR HOME-USERS

CROSS REFERENCE

The subject matter of this application is related to co-pending US application Ser. No. 12/807,481, filed Sep. 7, 2010, titled "Apparatus and Methods for Reuse of Injection Needle for Home Users" of Tara Chand Singhal.

FIELD OF THE INVENTION

A lancet device for reuse, of single-use disposable lancets for home-users, to reduce the cost of such disposables and to reduce the infrastructure cost of disposing sharp medical waste, is described.

BACKGROUND

Based on one statistic, there are approximately 34 million diabetic in United States. Nearly all of them would need to measure their blood glucose levels multiple times a day. To test blood glucose levels, a meter, a test strip and a lancet device to draw blood is required. The lancet device uses a single use disposable lancet.

Cost of use of such disposable lancets is borne by the health care system and ultimately the patient. The used lancets also create a medical waste disposal issue and require infrastructure for the safe disposable of the sharp medical waste.

Governments have come to realize the problem associated with safe disposable of sharp medical waste as the people on their own discard such waste in the household waste. Despite the growing problems associated with improper disposal of sharps outside health care facilities, there are no consistent regulations or guidelines for their safe disposal.

Current EPA guidelines, suggest disposing all sharps (needles, lancets, syringes) in a household plastic container or coffee can, secure the lid and write do not recycle on the outside and simply deposit in household trash.

Unfortunately, this does not take the needle out of the waste stream—it simply ends up in the general household trash putting neighbors, children and waste workers at risk of needle stick injuries.

Laws at State level have been enacted to address this problem. As an illustration of the magnitude of this problem of sharp medical waste disposal, following excerpts from a California law SB 1305 are quoted below.

SB 1305, Figueroa The Medical Waste Management Act.

This bill would, on or after Sep. 1, 2008, prohibit a person from knowingly placing home-generated sharps waste in certain types of containers, provide that home-generated sharps waste shall be transported only in a sharps container, as defined in the act, or other container approved by the department or local enforcement agency, and provide that this waste shall only be managed at specified locations consistent with existing law.

THE PEOPLE OF THE STATE OF CALIFORNIA DO ENACT AS FOLLOWS: SECTION 1. The Legislature finds and declares all of the following:

(a) The development of a safe, convenient, and cost-effective infrastructure for the collection of millions of home-generated sharps, and the public education programs to promote safe disposal of these sharps, will require a cooperative effort by the State Department of Health Services, the California Integrated Waste Management Board, local governments, large employers, dispensing pharmacies, as well as health care, solid waste, pharmaceutical industries, and manufacturers of sharps.

SEC. 2. Section 117671 is added to the Health and Safety Code, to read:

117671. "Home-generated sharps waste" means hypodermic needles, pen needles, intravenous needles, lancets, and other devices that are used to penetrate the skin for the delivery of medications derived from a household, including a multifamily residence or household.

SEC. 4. Section 118286 is added to the Health and Safety Code, to read:

118286. (a) On or after Sep. 1, 2008, no person shall knowingly place home-generated sharps waste in any of the following containers:

(1) Any container used for the collection of solid waste, recyclable materials, or green-waste.

(2) Any container used for the commercial collection of solid waste or recyclable materials from business establishments.

(3) Any roll-off container used for the collection of solid waste, construction, and demolition debris, green-waste, or other recyclable materials.

(b) On or after Sep. 1, 2008, home-generated sharps waste shall be transported only in a sharps container, or other containers approved by the enforcement agency, and shall only be managed at any of the following:

(1) A household hazardous waste facility pursuant to Section 25218.13.

(2) A "home-generated sharps consolidation point" as defined in subdivision (b) of Section 117904.

(3) A medical waste generator's facility pursuant to Section 118147.

(4) A facility through the use of a medical waste mail-back container approved by the department pursuant to subdivision (b) of Section 118245.

It is the objective of the embodiments herein to address the many problems associated with the use of lancets for the home-users as described above.

It is the objective to reduce the cost to the users directly and health care system indirectly of the disposable lancets for home use. It is yet another objective to make task of using lancets less cumbersome and with fewer steps. It is yet still another objective to reduce the cost of the infrastructure for disposing such sharp medical waste as required by the State laws.

SUMMARY

The problem associated with the use of prior art at-home lancets is summarized with reference to Prior Art FIG. 1. As illustrated in prior art FIG. 1, a pen like lancet device 10 has a lancet housing 12, a lancet plunger 14, a lancet 16, a lancet height adjustment mechanism 13, and a lancet cap 18, with an opening 20 for exposing lancet needle movement. The lancet 16 has a lancet base 16A and a lancet needle 16B affixed to the lancet base 16A.

There is illustrated also a box 22A of lancets with a supply of fresh lancets and a sharp medical waste container 22b for storing used lancets. Each time, a user needs to use the lancet device 10 the user retrieves a lancet 16 from the box 22A. After each use, the used lancets are discarded in the sharp medical waste container 22B

Before each use of the lancet device 10, the user removes the cap 18 from the lancet device 10, and inserts a fresh lancet 16 from the lancet box 22A into the lancet housing 12, and then removes a lancet needle protective cover from the lancet. The user then closes the cap 18 back on to the lancet device 10. The lancet device 10 is now ready for use.

The lancet device 10 with the help of plunger 14 is used to plunge the lancet 16 and expose the needle 16B through the opening 20 in the cap 18. The depth of exposure of the needle is calibrated with the calibration mechanism 13. After the lancet device 10 has been so used to draw blood, the cap 18 is again removed from the lancet device and the used lancet 16 is removed from the lancet housing 12. The used lancet 16 is discarded as sharp medical waste in the container 22B.

Many businesses make and sell lancet devices for use with their blood glucose meters. A brand of lancet device called Multiclix® uses a lancet drum in lieu of a single lancet. The lancet drum stores six individual needles. The lancet drum is used in the Multiclix lancet device, enabling the drum to be rotated and a fresh lancet to be plunged. After the six needles in the drum have been used, the cap 18 is opened, the drum is removed and discarded and a fresh drum is used from a package of drum supply.

As has been described in the background section and summarized above, there are three issues associated with the use of a lancet device that uses single use disposable lancets. One issue is the cost of the disposable lancets, the second issue, is the many steps that are required to use a disposable lancet, and the third issue is the cost of infrastructure for disposal of such sharp medical waste. The industry that manufactures these lancets and their lancet devices states a reason for not to reuse such single use lancets. The stated reason is the risk of infection from reuse.

The embodiments herein teach a lancet device that enables a large number of uses from a single lancet, uses numbering in hundreds, without having to remove and reload a lancet or a lancet drum for a home-user in the lancet device. The lancet device for each use of the lancet disinfects the lancet and prepares the lancet for reuse while it is stored in the lancet device.

Thus, the embodiments described herein alleviate many issues and concerns as identified above that of, (i) related to risk of infection and disposal of sharp medical waste, (ii) having to purchase a bulk supply of lancets, (iii) and the many steps required to load, reuse and discard used lancets.

These and other aspects of the embodiments are described in detail with the help of the accompanying drawings and the description.

BRIEF DESCRIPTION OF THE DRAWINGS

Some of the novel features of the embodiments will be best understood from the accompanying drawings, taken in conjunction with the accompanying description, in which similar reference characters refer to similar parts, and in which:

FIGS. 3A and 3B are block diagrams that illustrate features of a preferred embodiment of a cap of the lancet device for reuse of a lancet.

FIGS. 4A and 4B are block diagrams that illustrate features of a preferred embodiment of disinfectant disc and use of such a disc inside of a cap for reuse of a lancet.

FIG. 6 is a method diagram for a lancet reuse device.

DESCRIPTION

Introduction

Figure 1:
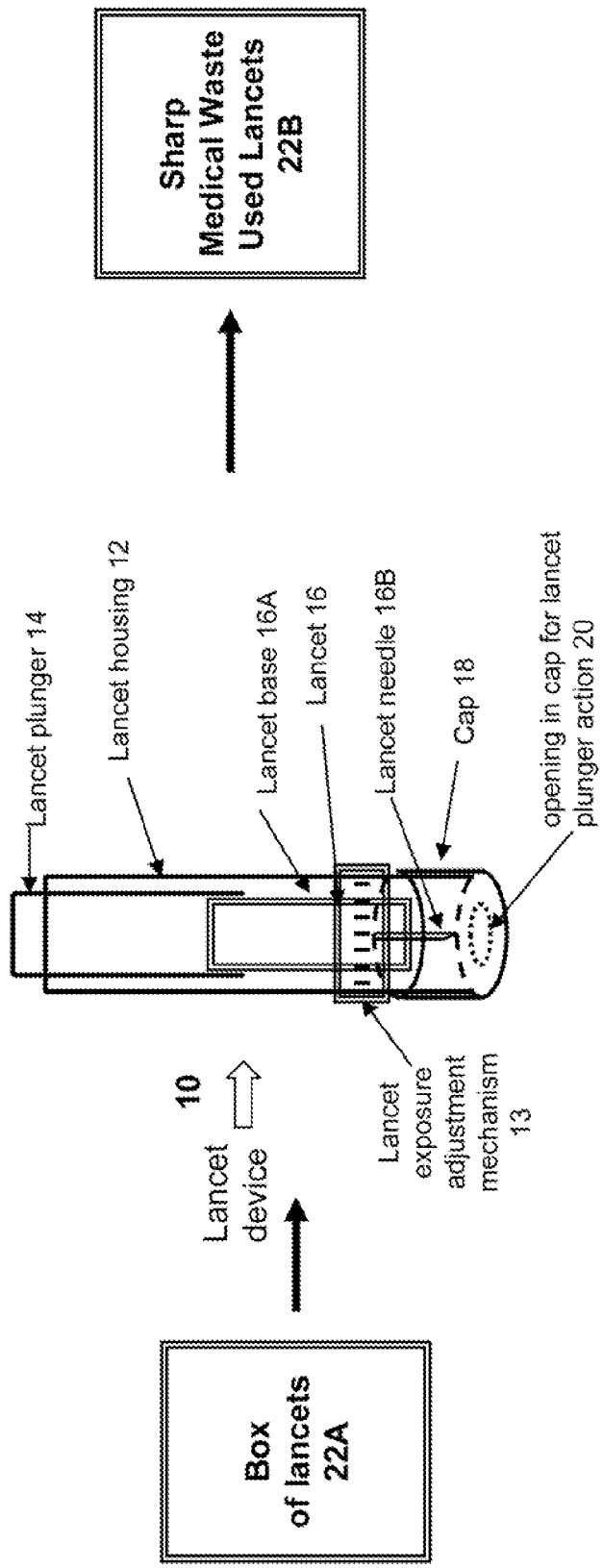
FIG. 1 is prior art block diagrams that illustrates features of the prior art for the use of lancet device and the lancets using single lancets.
Figure 2:
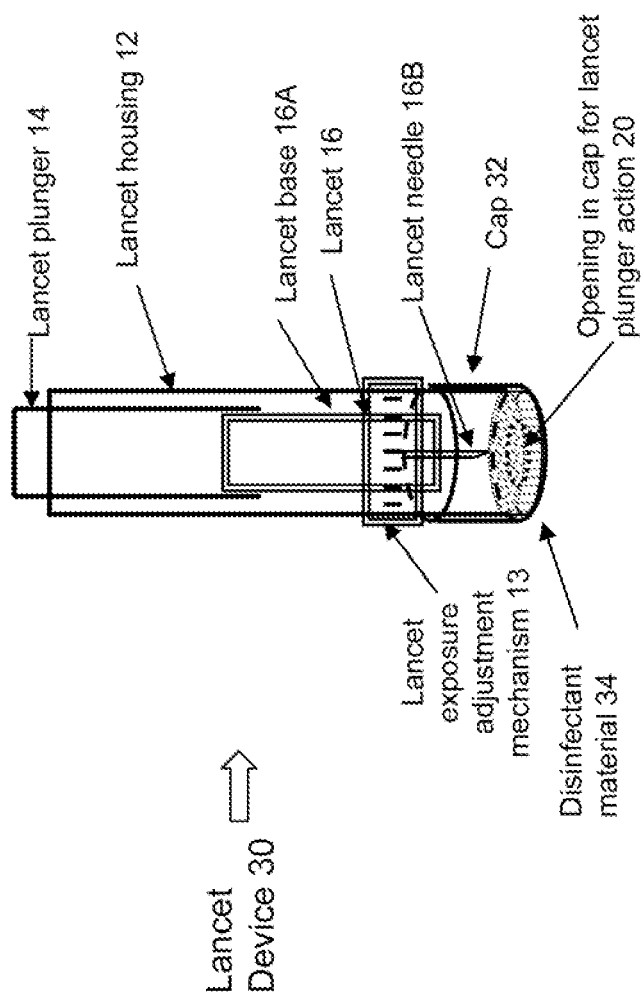
FIG. 2 is block diagram that illustrates features of a preferred embodiment of a lancet device for reuse of single use lancets.

FIG. 2 illustrate features of an embodiment of a lancet device 30. The lancet device 30 has a device cap 32 that positions a disinfectant material 34 within the cap 32.

FIG. 3A illustrates features of the lancet cap 32 for use with the lancet device 30. The lancet cap 32 has a disinfectant material 34 that is positioned in a part of the cap 32. FIG. 3B illustrate a view of the cap 32 with the disinfectant material 34 and a lancet needle 16B attached to the lancet base 16A immersed inside the disinfectant material 34.

FIG. 4A illustrate detailed views of the disinfectant 34, cap 32 and the lancet 16. The disinfectant material 34 may be in the form of a disc 36. FIG. 4B illustrates detailed views of a preferred structure of the disc 36.

Figure 5A:
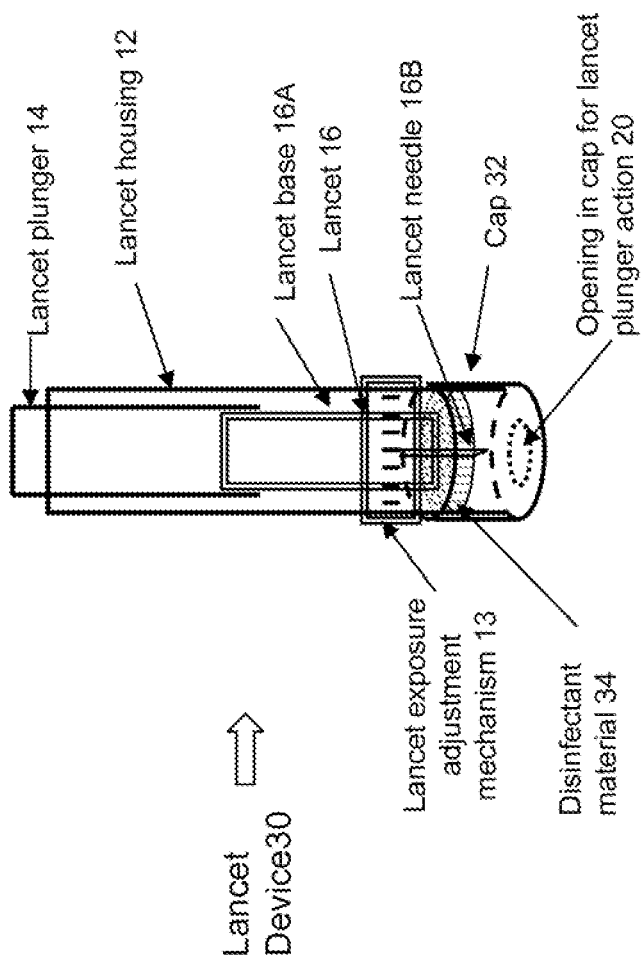
FIG. 5A is block diagram that illustrates features of a preferred embodiment of a lancet device with a built-in disinfection for each lancet use.
Figure 5B:
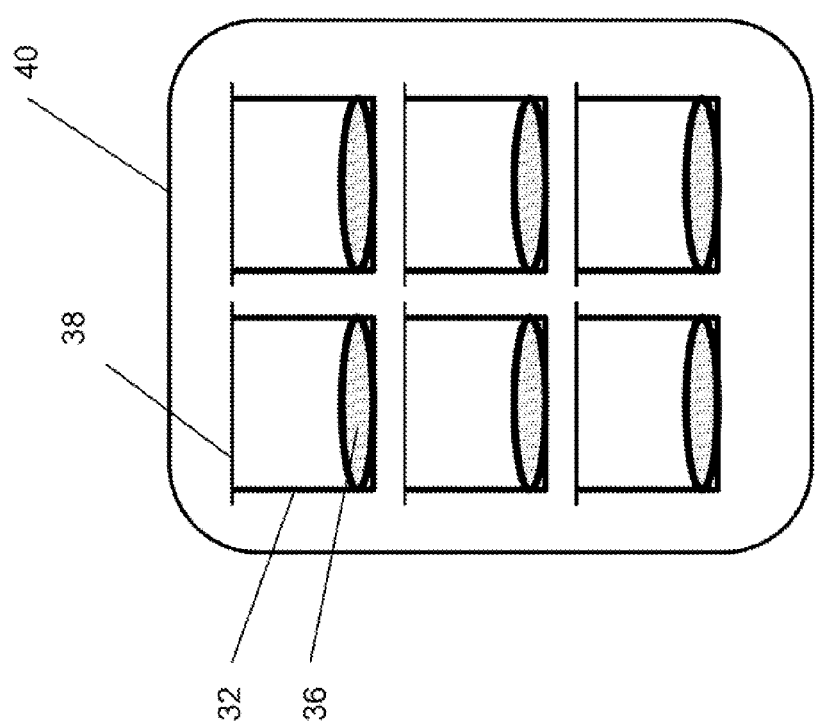
FIG. 5B is block diagram that illustrates features of a preferred embodiment of a cap with a disinfectant disc for use in a lancet device that may be sold in the market.
Figure 5D:
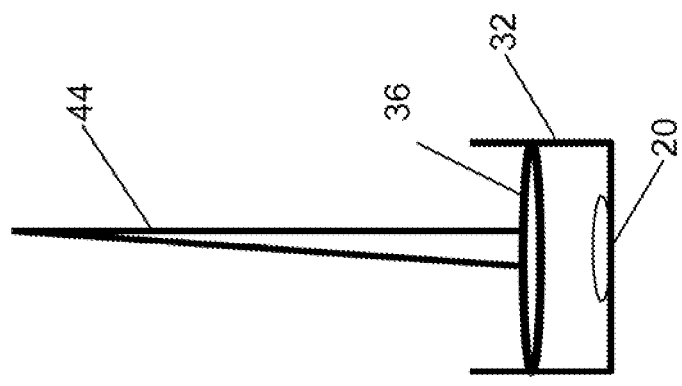
FIGS. 5C and 5D are block diagrams that illustrates features of a preferred embodiment for use of a disinfectant disc in a lancet device cap with the help of a tool that may be sold in the market.
Figure 5C:
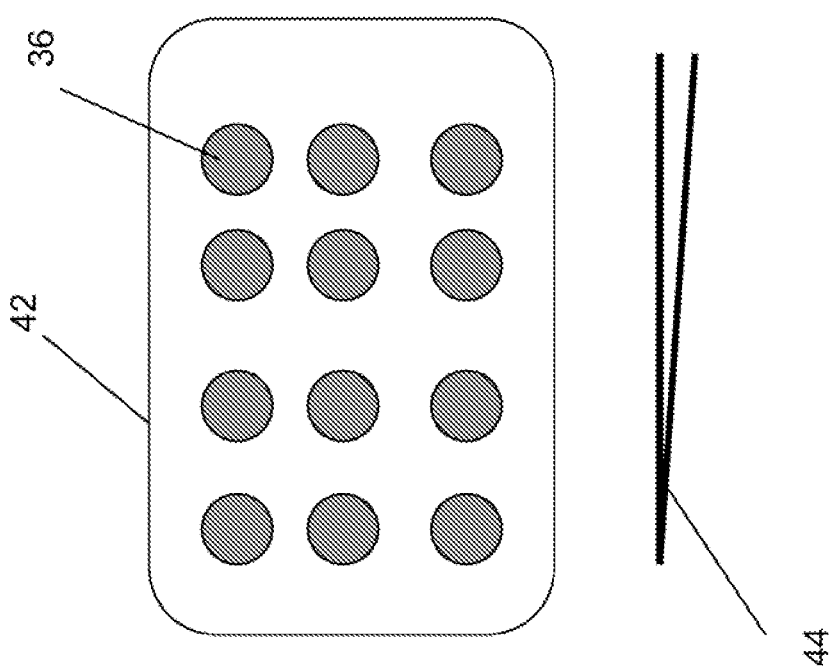

Three embodiments in how a lancet device 30 may be used and sold in the market are described with the help of FIGS. 5A, 5B, and 5C. FIG. 5A illustrates a sealed lancet device 30 with a built-in long lasting disinfection using disinfectant material 34 that disinfects the lancet for each use. After hundreds of uses, lasting over many months, the lancet device 30 may be discarded.

FIG. 5B illustrates how the lancet cap 32 may be packaged and sold in the after market. FIG. 5C illustrate how the disc 36 may be packaged and sold in the after market. FIG. 5D illustrate how the disc 36 may be removed from the packaging and inserted in the cap 32 therein with the help of a forceps like tool.

FIG. 6 illustrates a method for use of the lancet device 30. These and other features of the embodiments are described herein where the headings are provided for reader convenience.

Lancet Device 30

As illustrated in FIG. 2, the lancet device 30 used for drawing a blood sample for testing has a lancet 16, a lancet holding mechanism 12, a lancet activation plunger 14, a lancet height adjusting mechanism 13, and a removable lancet cap 32 with an opening 20 for touching against the human body.

The lancet 16 has a needle 16B, where the needle is movable inside the cap 32 with the lancet activation plunger 14. The lancet cap 32 has positioned inside the cap a disinfectant material 34 that disinfects the lancet needle for each use.

As illustrated in FIG. 3A, a prior art lancet cap 18 of a prior art lancet device 10 may be modified to a lancet cap 32 for use with lancet device 30. The lancet cap 32 for use in the lancet device 30 has a disinfectant material 34 positioned at the bottom of the cap 32. As illustrated in FIG. 3B, the disinfectant material 34 is made of sponge like material that holds a disinfectant and lets the needle move or rest inside the disinfectant material.

As illustrated in FIG. 4A view 37A, the lancet needle 16B rests outside the disinfectant material 34, when not plunged.

Alternatively, as illustrated in FIG. 4A, view 37B, the tip of the lancet needle 16B rests inside the disinfectant material 34, when not plunged. As illustrated in view 37C, the lancet needle 16B moves through the disinfectant material 34 when used, disinfecting the needle 16B for each use. As illustrated in FIG. 4B, the disinfectant material 34 may be in the form of a disc 36. The disc 36 is described later herein.

Disinfectant Material 34

The disinfectant material 34 may be in the form of a gel or a porous material that may be encased in a protective covering that allows the needle of the lancet to move inside it or through it when plunged. The industry provides many types of disinfectant material that are sold for different uses and applications, where the medium for holding the chemically active compound may be different mediums. One such medium is a gel that may be made in a consistency or density that it suitable for the application in a lancet device 32 as described herein. The disinfectant material 34 may be a dense cotton material suffused with a suitable disinfecting agent for this purpose. It may also be rubber like medium with disinfecting properties.

It is believed that the requirement to disinfectant the needle is not severe as the lancet device and the lancets it uses are a personal device and are used by a single user. That is, lancet device is not shared between users even in a home setting.

It is believed that a lancet device 30 may be used three to four times in a day or approximately 100 times in a month. It is believed that from a user desirability and practicality view point, the lancet device 30, with the material 34 would be used to disinfect the needle at least that many number of times. It would be further desirable, if the material would disinfect the lancet more than that such as for a three month or six month or a year's use. That would require the material 34 to be used for hundreds or 1000 times.

There may be different embodiments on how and where the disinfectant material 34 may be positioned inside the lancet device 30. In one embodiment, as shown in FIG. 5A, the material 34 may be made a part of the lancet itself; instead of positioning the material 34 inside the cap as in the preferred embodiment. In this embodiment, the material 34 may be incorporated in the lancet housing 12, as a lancet moves inside the housing 12 relative to the housing for a plunger action for the lancet. Other embodiments are possible and are not ruled out.

In this form of packaging, as shown in FIG. 5A, a throw away lancet device 30 that is good for a year's worth of use may be sold.

Disinfectant Disc 36

As illustrated in FIG. 4B, the disinfectant material 34 may be in the shape of a disc 36 that is positioned inside the cap 32. The disinfectant material 34 is in the shape of a disc 36 that is positioned inside the cap 32 at the bottom part of the cap. The thickness of the disc 36 may be at least 0.5 mm to 3 mm thick that positions a part or the entire needle 16B inside the disc 36. The thickness of the disc 36 may be any other size in thickness that would be suitable for positioning the disc 36 in any part of the lancet device 30 so that it can be used for disinfecting the needle 16B permanently or for each use. The diameter of the disc 36 may be any size suitable for placing inside the lancet device or cap.

The thickness of the disinfectant disc or layer is a function of the length of the lancet needle and how the depth of the needle movement for a plunger action. These two aspects of the lancet needle 16 and the lancet device 30 may be adjusted to work with the lancet device 30. It is believed that the disinfect disc or layer may be ½ mm to 3 mm thick.

The disinfectant material 34 may have a medium in the form of a gel or other suitable density medium that stays confined in the stack and when the needle is pushed through it, the stack disinfects the needle. The stack may be a dense cotton material suffused with a suitable disinfecting agent for this purpose. It may also be rubber like medium with disinfecting properties.

Depending on the type of disinfectant material 34 and how it is packaged such as in the form a disc 36, the material 34 may be used to disinfect the needle at least 100 times and perhaps a 1000 or more times. That, it is believed, provides for a great convenience and cost savings to a user as well as drastically reduces the disposal of sharp medical waste.

As illustrated in FIG. 4B, the disc 36, may have a butyl rubber membrane 36A at the bottom of the disc to separate the material 34 from the cap 32 surface. The butyl rubber membrane 36A may be used to clean the needle of any material 34 residue. The butyl rubber membrane may be a thickness suitable for this purpose and may be 0.5 mm thick. The material 34 in the disc 36 may be further packaged in a wrapper that would keep the shape of the disc enabling each disc to be removed and inserted from the cap 32.

As illustrated in FIG. 5B, a supply of caps 32 with discs 36 pre-inserted in the cap 32 and a protective cover 38 applied to the cap 32 may be sold in a package 40 for after market use with the lancet device 30. A user would remove a cap 32 from the package 40 and use in a lancet device 30.

Alternatively, as illustrated in FIG. 5C, a supply of disc 36 may be sold in the aftermarket in an air sealed package 42. As illustrated in FIGS. 5C and 5D, a forceps like tool 44 may be provided with the supply that may be used to remove the old disc 36 from the cap 32 and insert a new replacement disc 36 in the cap 32.

The use of these disposable lancets is confined to a home-user. They are not meant for or used between different users. Therefore, the risk of infection from one user to the next user or between users is not present. Hence, the risk of infection from reuse of lancets for the reasons as above is negligible. That risk is further negligible or non-existent, specifically after the lancet needle has been sanitized and disinfected by the material 34 and the disc 36.

The number of reuses of a lancet with the material 34 may be limited to the quantity of the test strips at hand. The quantity of test strips may be 50, or 100. Hence for an average user, the lancet reuse number in a month is approximately 90 reuses. The reuse of cap 32 with material 34 may be limited to reuses of up to 100 maximum.

The reuse may be limited to any number less than 100, such as 20, 35, or 50 etc. The number of reuses of a lancet needle in a cap 32 with material 34 that may be limited to is believed, to be a function of the selection of the material 34 and its disinfecting properties.

As illustrated with the help of FIG. 5B, a supply of replacement caps 32 may be sold in the aftermarket. If a lancet is reused 100 times with the cap 32, then it would lead to a reduction in the use of disposable needles and the corresponding cost of disposing sharp medical waste one hundred fold. If the cap 32 enables the lancet to be reused 25 times, a corresponding 25 fold reduction in the cost of disposable lancets and sharp medical waste is expected.

Alternatively, as illustrated in FIG. 5C, what may be sold in the aftermarket may be a supply of disc 36 that can be inserted in the cap 32. The user may remove individual disc 36 from the packet and insert inside the cap 32 with the help of a tool. Such a tool resembling a forceps may be used to both remove the disc 36 from the packing and then insert inside the cap 32 and push to the bottom of the cap 32. The tool would also be used to remove the old disc 34 from the cap 32, before a new disc 36 is inserted in the cap.

A lancet device has a lancet, a lancet holding mechanism, a lancet activation plunger, and a lancet cap with an opening for touching against the human body. The lancet has a needle, where the needle is movable inside the cap with the lancet activation plunger. A disinfectant material is positioned inside the lancet device or as part of the lancet device that disinfects the needle for each use of the lancet.

The disinfectant material is made of sponge like material that holds a disinfectant and lets the needle move or rest inside the disinfectant material.

In one embodiment as had been illustrated with the view 37B of FIG. 4A, the lancet needle tip rests inside the disinfectant material, when not plunged, disinfecting the needle between each use. Alternatively, as illustrated with the view 37C of FIG. 4A, the lancet needle moves through the disinfectant material when used, disinfecting the needle for each use.

The lancet cap has positioned inside the cap a disinfectant material, disinfecting the lancet needle for each use. The disinfectant layer or disc 36 disinfects the needle, as the needle is plunged through the cap.

Method of Operation

A method for a lancet device 30 is illustrated with the help of FIG. 6, where all the steps may not be used or used in the order specified. The method for a lancet device used for drawing blood sample for testing having the lancet device with a lancet, a lancet holding mechanism, a lancet activation plunger, and a removable lancet cap with an opening for touching against the human body, having the lancet with a needle, where the needle is movable inside the cap with the lancet activation plunger comprising the steps of:

At step 100, positioning, inside the lancet cap, a disinfectant material, disinfecting the lancet needle for each use.

At step 102, making the disinfectant material, of sponge like material, for holding a disinfectant and for moving or resting the needle, inside the disinfectant material.

At step 104, resting the lancet needle inside the disinfectant material, when not plunged, disinfecting the needle between each use, alternatively:

At step 106, moving the lancet needle through the disinfectant material when used, disinfecting the needle for each use.

At step 108, shaping the disinfectant material as a disc for positioning inside the cap.

At step 110, shaping the disinfectant material as a disc for positioning inside the cap, where the thickness of the disc is at least a 1 mm to 3 mm thick for positioning and moving the needle inside the disc.

At step 112, shaping the disinfectant material as a disc and positioning the disc inside the cap at the bottom of the cap.

In summary, the preferred embodiments are for an apparatus and method for a lancet device that enables lancet reuse in a lancet device for multiple reuses numbering in hundreds for a same home-user drawing blood for use with a test strip for blood glucose measurement. The lancet device has a disinfecting agent that is positioned inside the lancet device. The agent disinfects a single-use lancet needle for reuse when the needle is stored in and is moved inside the lancet device.

The embodiments described herein alleviate many issues and concerns as identified related to use of lancets for home-users such as those (i) related to risk of infection, (ii) cost of infrastructure for disposal of sharp medical waste, (ii) cost of having to purchase a bulk supply of lancets, (iv) and the many steps required to load, reuse and discard single use lancets.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

What is claimed is:

1. A lancet device used for drawing blood sample for testing comprising:
   a. the lancet device has a lancet, a lancet holding mechanism, a lancet activation plunger, and a lancet cap with an opening for touching against the human body, the lancet has a needle, where the needle is movable inside the cap with the lancet activation plunger;
   b. a disinfectant material is positioned inside the lancet device or as part of the lancet device that disinfects the needle for each use of the lancet.

2. The device as in claim 1, comprising:
   the disinfectant material is made of sponge like material that holds a disinfectant and lets the needle move or rest inside the disinfectant material.

3. The device as in claim 1, comprising:
   the lancet needle rests inside the disinfectant material, when not plunged, disinfecting the needle between each use.

4. The device as in claim 1, comprising:
   the lancet needle moves through the disinfectant material when used, disinfecting the needle for each use.

5. The device as in claim 1, comprising:
   the disinfectant material is positioned inside the cap, disinfecting the lancet needle for each use.

6. The device as in claim 5, comprising:
   the disinfectant material is in the shape of a disc that is positioned inside the cap.

7. The device as in claim 6, comprising:
   the disinfectant material is in the shape of a disc that is positioned inside the cap, the thickness of the disc is at least a 1 mm to 3 mm thick and positions the needle inside the disc.

8. A method for a lancet device used for drawing blood sample for testing comprising the steps of:
   a. having the lancet device with a lancet, a lancet holding mechanism, a lancet activation plunger, and a removable lancet cap with an opening for touching against the human body, having the lancet with a needle, where the needle is movable inside the cap with the lancet activation plunger;
   b. positioning a disinfectant material inside the lancet device, disinfecting the lancet needle for each use.

9. The method for device as in claim 8, comprising the steps of:
   making the disinfectant material of sponge like material for holding a disinfectant and for moving or resting the needle inside the disinfectant material.

10. The method for device as in claim 8, comprising the steps of:
    resting the lancet needle inside the disinfectant material, when not plunged, disinfecting the needle between each use.

11. The method for device as in claim 8, comprising the steps of:

moving the lancet needle through the disinfectant material when used, disinfecting the needle for each use.

12. The method for device as in claim 8, comprising the steps of:
shaping the disinfectant material in the form of a disc, for positioning inside the lancet cap, as a disinfectant material that is used for disinfecting the lancet needle for each use.

13. The method for device as in claim 8, comprising the steps of:
shaping the disinfectant material as a disc for positioning inside the cap, where the thickness of the disc is at least a 1 mm to 3 mm thick for positioning and moving the needle inside the disc.

14. The method for device as in claim 8, comprising the steps of:
shaping the disinfectant material as a disc and positioning the disc inside the cap at the bottom of the cap.

15. A lancet device used for drawing blood sample for testing, has a lancet, a lancet holding mechanism, a lancet activation plunger, and a removable lancet cap with an opening for touching against the human body, the lancet has a needle, where the needle is movable inside the cap with the lancet activation plunger, comprising:
the lancet cap has positioned inside the cap a disinfectant material, disinfecting the lancet needle for each use.

16. The device as in claim 15, comprising:
the disinfectant material is made of sponge like material that holds a disinfectant and lets the needle move or rest inside the disinfectant material.

17. The device as in claim 15, comprising:
the lancet needle rests inside the disinfectant material, when not plunged, disinfecting the needle between each use, alternatively the lancet needle moves through the disinfectant material when used, disinfecting the needle for each use.

18. A method for a lancet device used for drawing blood sample for testing having the lancet device with a lancet, a lancet holding mechanism, a lancet activation plunger, and a removable lancet cap with an opening for touching against the human body, having the lancet with a needle, where the needle is movable inside the cap with the lancet activation plunger comprising the steps of:
positioning inside the lancet cap a disinfectant material, disinfecting the lancet needle for each use.

19. The method for device as in claim 18, comprising the steps of:
making the disinfectant material of sponge like material for holding a disinfectant and for moving or resting the needle inside the disinfectant material.

20. The method for device as in claim 18, comprising the steps of:
a. resting the lancet needle inside the disinfectant material, when not plunged, disinfecting the needle between each use, alternatively:
b. moving the lancet needle through the disinfectant material when used, disinfecting the needle for each use.

* * * * *